United States Patent [19]

Adams

[11] Patent Number: 4,588,979

[45] Date of Patent: May 13, 1986

[54] ANALOG-TO-DIGITAL CONVERTER

[75] Inventor: Robert W. Adams, Acton, Mass.

[73] Assignee: DBX, Inc., Newton, Mass.

[21] Appl. No.: 658,399

[22] Filed: Oct. 5, 1984

[51] Int. Cl.[4] .......................................... H03K 13/02
[52] U.S. Cl. ................... 340/347 AD; 364/724
[58] Field of Search ............... 340/347 AD, 347 DD; 364/724

[56] References Cited

U.S. PATENT DOCUMENTS

| 3,732,409 | 5/1973 | Fletcher et al. | 235/164 |
|---|---|---|---|
| 3,906,218 | 9/1975 | Nussbaumer | 235/156 |
| 3,959,637 | 5/1976 | Nussbaumer | 235/152 |
| 3,988,607 | 10/1976 | Eggermont et al. | 235/156 |
| 4,020,332 | 4/1977 | Crochiere et al. | 235/152 |
| 4,021,616 | 5/1977 | Betts | 179/15 RV |
| 4,032,914 | 6/1977 | Candy et al. | 340/347 AD |
| 4,074,069 | 2/1978 | Tokura et al. | 179/15 C |
| 4,101,964 | 7/1978 | Betts | 364/724 |
| 4,167,731 | 9/1979 | Eggermont | 340/347 DD |
| 4,270,026 | 5/1981 | Shenoi et al. | 179/15.55 R |
| 4,281,318 | 7/1981 | Candy et al. | 340/347 AD |
| 4,285,045 | 8/1981 | Tamori et al. | 364/724 |
| 4,302,631 | 11/1981 | Shenoi et al. | 364/724 |
| 4,308,524 | 12/1981 | Harrison et al. | 340/347 AD |
| 4,344,149 | 8/1982 | van der Meeberg | 364/724 |
| 4,352,162 | 9/1982 | Nyuji et al. | 364/724 |
| 4,356,558 | 10/1982 | Owen et al. | 364/724 |
| 4,419,190 | 5/1983 | Flanagan et al. | 364/513.5 |
| 4,419,686 | 12/1983 | Morrison | 358/13 |
| 4,435,823 | 3/1984 | Davis et al. | 375/14 |

Primary Examiner—Vit W. Miska
Attorney, Agent, or Firm—Schiller & Pandiscio

[57] ABSTRACT

A device is disclosed for converting an input signal to a digital output signal at a preselected sampling rate with an increase in dynamic range without aliasing. The preferred embodiment utilizes a converter for producing a low resolution digital signal at a higher frequency and an averaging digital filter arrangement for increasing the resolution at the preselected sampling rate. The device is easily capable of producing digital output signals of at least 17 bits at any frequency such as 48 KHz.

21 Claims, 29 Drawing Figures

ANALOG-TO-DIGITAL CONVERTER

The present invention relates generally to analog-to-digital (A/D) converters, and more particularly, to an improved A/D converter having greater output resolution than most prior art converters, while minimizing aliasing. The converter is particularly adapted for processing audio signals, although the converter can easily be used with other types of signals.

Most commercially-available analog-to-digital converters are design-limited so that they can only provide digital output signals having a maximum of 16 bits of output resolution. Thus, any analog signal applied to the input of such converters can be represented by a digital signal having a maximum of 65,536 (2 to the 16th power) different values. The rounding of an analog input signal into discrete number values of limited precision is called "quantization" and in practical terms, results in the addition of noise and distortion to the processed signals. A 16-bit converter provides a theoretical 96 dB dynamic range, although in practice typical 16-bit converters provide at best only 90 dB dynamic range.

These A/D converters are limited to a maximum 16-bit resolution for many reasons, which will be more apparent in connection with FIG. 1. FIG. 1 shows a typical converter of the successive approximation type. The analog input signal is first applied to an "anti-aliasing" filter 30 which removes all portions of the input signal above one-half the sampling frequency (for audio signals the sampling frequency is typically 48 KHz). This filter typically has a very flat frequency response up to 20 KHz, the usual bandwidth of interest in audio applications, and will attenuate portions of the signal above 24 KHz, by at least 60 dB. The filter 30 also preferably has a flat phase response so that any time delay introduced by the filter will be constant with frequency.

The output of filter 30, still an analog signal, is applied to sample and hold circuit 32 which samples the filter output at the sampling rate and "holds" it during the sampling period while the actual conversion takes place. To guarantee accuracy, the signal held by the circuit 32 must not vary more than plus or minus one part in approximately 130,000 (twice the total number of discrete values) during each sample period.

The A/D conversion of each sample held by circuit 32 is provided by the successive approximation converter 34. The latter includes a 16-bit D/A (digital-to-analog) converter 36 used to generate "test" signals to signal comparator 38. The latter compares the test signals with the sampled output of circuit 32 to generate a signal to the successive approximation circuit 40. The latter operates with the D/A converter 36 through 16 different approximations to provide the quantized binary output of the A/D converter, the output of which is applied to the output latch 42. Once the 16-bit quantization process is completed, the latch is clocked to provide the 16-bit digital signal at output 44.

More specifically, the analog input signal is filtered by filter 30 and applied to circuit 32. The latter holds the analog value received at the beginning of the sampling interval for the duration of that interval. At the beginning of the interval, one-half the maximum signal is first provided by the D/A converter 36 to the negative input of comparator 38. If the sample is between zero and one-half the maximum value, the output of comparator 38 will be negative and the most significant bit of the binary output signal provided by converter 34 will be low. Alternatively, if the sample value is greater than one-half the maximum, the comparator will provide a positive signal and the most significant bit of the output of converter 34 will be high. Once the state of the most significant bit of the output is determined, the next-most significant bit is then determined, wherein the D/A converter 36 generates a signal to the comparator 38 which is equal to the median value of the range determined by the previous approximation. Specifically, if the previous approximation indicated that the value of the signal is between zero and one-half the maximum value, the second signal applied from D/A converter 36 to comparator 38 during the sampling interval will be one-quarter the maximum value. If the previous approximation indicated the value of the signal is between one-half and the maximum value, the signal applied by the converter 36 will be three-quarters the maximum value. When the signal from circuit 32 and applied to the positive input of comparator 38 is greater than the second signal applied by the D/A converter 36, then the comparator output will be positive. Alternatively, if the sampled value is less than the signal applied by converter 26, then the comparator output will be negative. This will determine the second-most significant bit of the 16-bit output. The process will continue during the sampling interval for a total of 16 successive approximations, each time reducing the range of approximation by one-half so as to provide a 16 binary bit signal to latch 42. Once the 16-bit signal is determined, the latch can be enabled at the end of the sampling interval to provide the digital signal to the output 44.

There are several reasons why the conversion procedure of this A/D converter cannot be easily extended beyond 16 bits of resolution. The first is that D/A converters (for use as converter 36) that are fast and accurate to 17 or more bits are not yet commercially available at any cost. Such converters typically employ resistors formed in an "R–2R" ladder and thus the largest resistor must be matched to the other resistors within a tolerance of $+/-1/64000$ for 16 bits. For 17 bits, the largest resistor would have to be matched within a tolerance of $+/-1/128000$ and for 18 bits a match within a tolerance of $+/-1/256000$ must be achieved. Finding commercially available resistors with values within the latter two tolerances is extremely difficult, if not impossible, to achieve.

Another problem with increasing the resolution of the FIG. 1 converter lies with the comparator 38. If the maximum signal input is 10 volts (a typical input for audio applications), the smallest increment for a 16-bit converter will be approximately 200 microvolts. If the sampling rate is 48 KHz, it is necessary to carry out each sample conversion with the converter 34 in approximately 20 microseconds. Each incremental approximation must, therefore, be carried out in approximately 1.2 microseconds. In each incremental step, it may take, for example, about 800 nanoseconds for the converter 36 to settle and the comparator 38 needs the remaining 400 nanoseconds to produce an output. Increasing the number of bits, therefore, requires the comparator 38 to respond to increments smaller than 200 microvolts. However, the typical comparator usually cannot switch fast enough (within the 400 nanoseconds) with an overdrive of less than 200 microvolts ("overdrive" being the difference between the signal inputs at the input terminals of the comparator). The smaller the difference between inputs, the greater the amount of time required for a given comparator to switch. Further, the comparator noise must be less than 200 microvolts peak-to-peak which is difficult to accomplish, particularly at the speed required for signal conversion.

Another difficulty in extending the successive approximation converter of FIG. 1 beyond a 16-bit resolution, is that the settling time of the D/A converter 36 is typically exponential. Increasing the number of bits to 17 or more, requires a non-linear (exponential) increase in settling time, which may make it impossible to achieve the required conversion time.

Another obstacle to increasing the resolution of the A/D converter shown in FIG. 1 beyond 16 bits is that the sample and hold circuit 32 will be required to hold the sample value within an even smaller tolerance of 1 part in about 260,000 for 17-bit resolution and 1 part in about 520,000 for 18-bit resolution.

Finally, the anti-aliasing filter 30 represents a formidable design problem, regardless of the resolution of the converter, and requires the use of expensive high-precision components.

It is, therefore, an object of the present invention to substantially reduce or overcome the problems asssociated with the prior art A/D converters of the type described with respect to FIG. 1.

Another object of the present invention is to provide an A/D converter easily capable of providing resolution greater than 16 bits.

Another object of the present invention is to provide a converter providing fast and accurate conversion of an analog signal to a digital signal without aliasing.

These and other objects are acheived by an improved device for converting an analog input signal to a digital output signal at a preselected sampling rate with an increase in dynamic range without aliasing. The preferred embodiment utilizes a converter for producing a low resolution digital signal at a higher sampling frequency and a digital filter arrangement for increasing the resolution at the preselected sampling rate.

Other objects of the invention will in part be self-evident and will in part appear hereinafter. The invention, accordingly, comprises the apparatus prossessing the construction, combination of elements, and arrangement of parts which are exemplified in the following detailed disclosure, and the scope of the application of which will be indicated in the claims.

For a fuller understanding of the nature and objects of the present invention, reference should be had to the following detailed description taken in connection with the accompanying drawings, wherein:

FIGS. 2A and 2B are respectively graphical representations of an exemplary analog signal and its frequency domain from 0 to 20 KHz;

Figure 2:
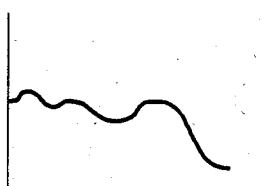
FIG. 2 is a graphical representation of a timing diagram associated with the operation of the circuit shown in FIG. 22.
Figure 2:
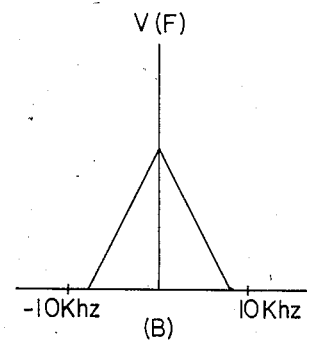
Figure 3:
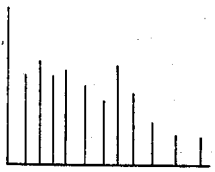
FIGS. 3A and 3B are respectively graphical representations of the train of weighted impulses provided by sampling the analog signal of FIG. 2A at 50 KHz and the frequency spectrum of the sampled signal.
Figure 3:
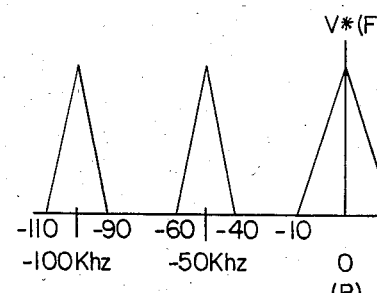

In order to have a better understanding of the present invention, a review of sampling theory is believed to be beneficial. Referring specifically to FIG. 2, an exemplary analog signal V(t) is shown in FIG. 2A with a frequency domain representation V(f) shown in FIG. 2B. It should be noted that in the example, V(f) has no energy above 10 KHz. If the signal V(t) is sampled at 50 KHz, i.e., the amplitude of V(t) is periodically determined 50,000 times per second, the time waveform V*(t) takes on the appearance of a train of weighted impulses (50,000 per second), as shown in FIG. 3A. The frequency spectrum V*(f) of the sampled signal, as shown in FIG. 3B, will include the original specturm V(f), as well as the same spectrum mirrored around every multiple of the sampling rate or frequency. The original continuous signal V(t) could be recovered completely from V*(t) if the mirrored spectral components above 10 KHz are removed using, for example, an appropriate low-pass filter.

If, however, the sampling rate is closer to the frequency spectrum of the original analog signal, a different result occurs. For example, if the original signal V(t) has spectral components V(f) up to 100 KHz, as shown in FIGS. 4A and 4B, and the signal is sampled at 100 KHz to provide the train of weighted impulses V*(t), shown in FIG. 5A, the original spectrum and the mirrored spectrum will overlap producing the phenomenon known as "aliasing", as shown by the shaded overlapping areas in FIG. 5B. Aliasing prevents the recovery of the original signal by low-pass filtering because of the presence of the energy from the mirrored spectrum within the spectral range of the original signal.

Figure 4:
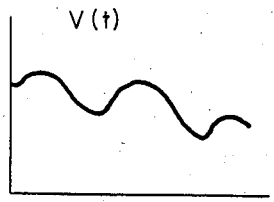
FIGS. 4A and 4B are respectively graphical representations of an exemplary analog signal and its frequency domain from 0 to 100 KHz.
Figure 4:
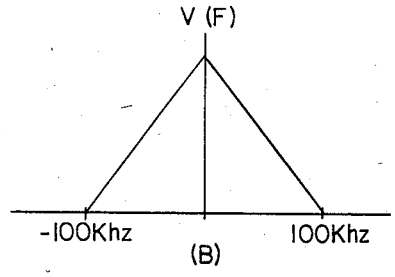
Figure 5:
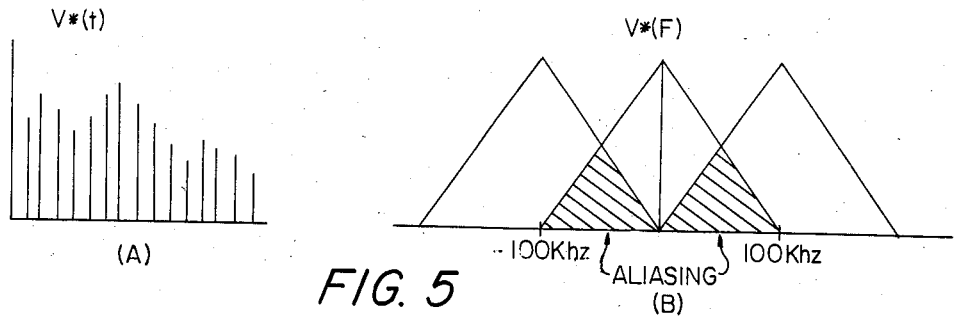
FIGS. 5A and 5B are respectively graphical representations of the train of weighted impulses provided by sampling the analog signal of FIG. 4A at 100 KHz and the frequency spectrum of the sampled signal.
Figure 6:
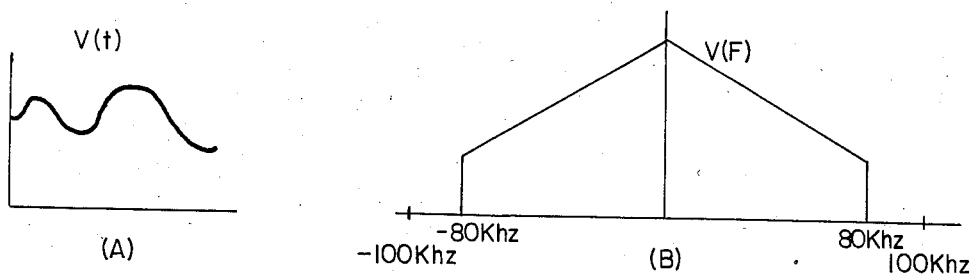
FIGS. 6A and 6B are respectively graphical representations of the analog signal and frequency domain of the signal of FIG. 4A filtered to remove components above 80 KHz.
Figure 7:
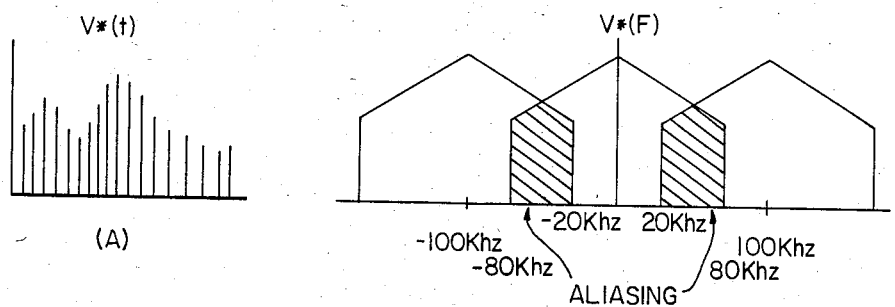
FIGS. 7A and 7B are respectively graphical representations of the train of weighted impulses provided by sampling the analog signal of FIGS. 6A and 6B at 100 KHz and the frequency spectrum of the sampled signal.

A simple approach of eliminating aliasing below the 20 KHz region of the spectrum shown in FIG. 5B is illustrated by the graphical representations shown in FIGS. 6 and 7. In particular, if the original signal V(t) of FIG. 4 is filtered so as to remove all of the signal energy above 80 KHz, as illustrated by the V(f) function shown in FIG. 6B, when the signal is then sampled at 100 KHz, aliasing will occur between 20 KHz and 50 KHz, while leaving the region between 0 and 20 KHz unaffected. Thus, the 0–20 KHz region can be recovered by low-pass filtering.

In summary, therefore, as a general rule, in order to avoid aliasing altogether, the sampling rate must be at least twice the highest frequency component present in the analog input signal. If, however, it is desirable only to avoid aliasing below some frequency W, and the sample rate is Fs, then it is only necessary to remove those spectral components of the signal before sampling that lie between N·Fs+W and N·Fs−W, where N is any integer so as to represent each multiple of the sampling rate. Thus, in the examples of FIGS. 6 and 7, where W=20 KHz and Fs=100 KHz, it is clear that the spectral components to be eliminated are between 80 KHz and 120 KHz, for N=1. A distinction between these two concepts of complete elimination of aliasing and elimination of aliasing within the bandwidth of interest will be helpful in understanding the present invention.

Figure 1:
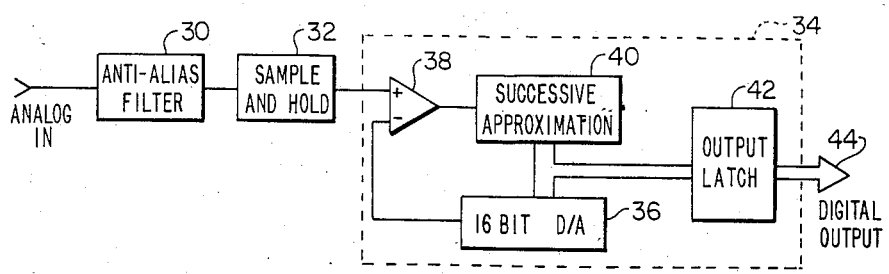
FIG. 1 is a block diagram of the prior art A/D converter, previously described.

In accordance with the present invention, an approach, referred to as "over sampling", is used to increase, if desired, the resolution of the converter of the present invention beyond the current 16-bit resolution maximum achieved with the A/D converter of the type shown in FIG. 1.

Figure 8:
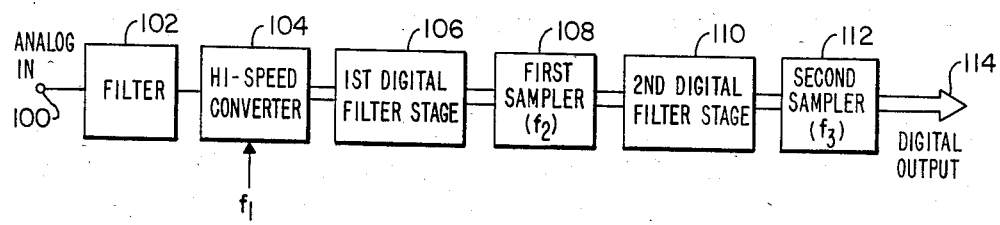
FIG. 8 is a block diagram of the preferred embodiment of the present invention.

The preferred embodiment of the present invention, shown in FIG. 8, comprises an input terminal 100 for receiving the analog input signal and connected to the input of an analog filter 102. The purpose of the latter will become more apparent hereinafter. The output of filter 102 is connected to an A/D converter 104 for providing a first digital signal of relatively low resolution (e.g., 4 to 6 bits) representative of the analog signal output of the filter 102 at a relatively fast digital word repetition or sampling rate f, (e.g., 6.144 MHz). This digital signal output of converter 104 will also contain a relatively large amount of noise energy, although the noise energy will be spread over a wide frequency spectrum as a result of the high-speed sampling rate. The spectral region of interest, e.g., the audio region of 20–20 KHz, compared with the sampling rate, is small, and, therefore, the actual amount of noise contained in this region will be relatively small. Due to the low resolution, the converter circumvents the need for extreme accuracy required by the conventional successive-approximation approach of the FIG. 1 converter.

Since the bit rate, i.e., the number of bits/second, produced by converter 104 is extremely high (e.g., the bit rate of a 4-bit converter running at 6 MHz is 24 megabits/second) compared to the typical bit rate of the conventional FIG. 1 converter (typically 800 kilobits/second) running at a typical sample or word rate (e.g., 48 KHz), the output of converter 104 cannot be used in most applications, where higher resolution at a 48 KHz rate is required. Accordingly, the output of converter 104 is connected to digital filter means, preferably a two-stage digital filter comprising filters 106 and 110 and samplers 108 and 112, for reducing the bit rate of the digital output signal at 114 to the desired speed, while increasing the resolution of the digital signal representative of the analog input signal within the bandwidth of interest. Filters 106 and 110 and samplers 108 and 112 are, therefore, used to convert the high-speed, low resolution output of the converter 104 to produce a slower, yet higher resolution digital output.

Figure 9:
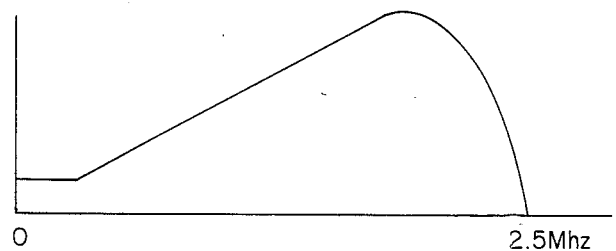
FIGS. 9–12 illustrate how digital filtering can reduce the bit rate of a digital signal so as to improve the resolution of the digital signal.
Figure 10:
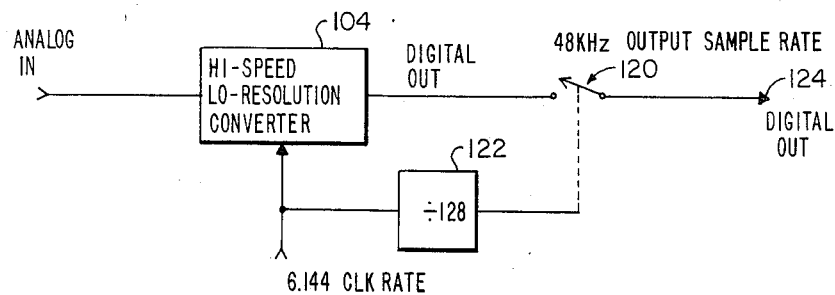
Figure 11:
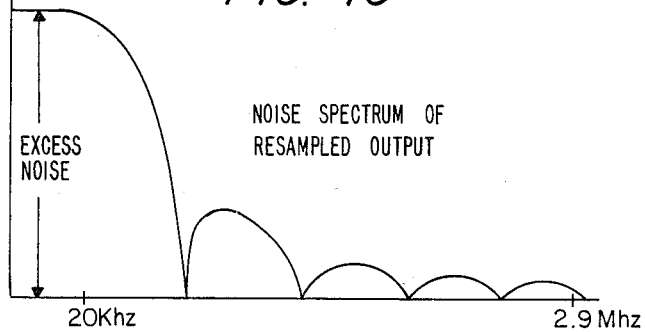

FIGS. 9–12 illustrate in greater detail how digital filtering can reduce the sampling rate of the signal output of converter 104 while increasing the resolution. FIG. 9 shows the typical noise spectrum of converter 104 (of the type shown in FIGS. 15 and 16) sampled at 6.144 MHz. As can be readily seen from this illustration, the total noise energy integrated over the entire bandwidth, e.g., 0–2.5 MHz, is quite high and spread over a wide frequency range, while the portion of the energy in the audio band, e.g., 0–20 KHz, is relatively low. If, as shown by the block diagram of FIG. 10, the bit rate of the output of converter 104 were reduced to the desired 48 KHz speed by taking 1 out of every 128 samples with the sampler 120 by using the divide-by-one-hundred-twenty-eight unit 122, the rules of sampling theory will apply. Thus, all of the noise components above 24 KHz will alias, resulting in large amounts of excess noise below 20 KHz in the sampled output of sampler 120, as shown in FIG. 11. Accordingly, one function of digital filters 106 and 110 and samplers 108 and 112 of FIG. 8 is to prevent aliasing by the noise components above 24 KHz and, therefore, prevent excess noise from being created below 20 KHz in the output at 114.

Figure 12:
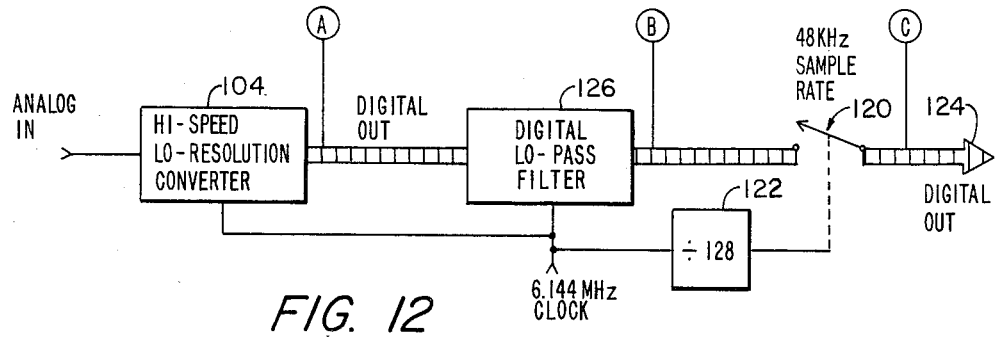

Referring to FIG. 12, the use of a single digital low-pass filter 126 is illustrated, wherein filter 126 is connected between the output of the converter 104 and the sampler 120 and is theoretically designed to remove all components of the input above 24 KHz so as to prevent aliasing of the noise from occurring. The process of reducing the sampling rate to the desired rate using digital filtering techniques can also increase the word length of the output sample and reduce the total noise energy of the digital output of converter 104. For audio applications, this digital filter, while satisfactory for many applications, is believed to be impossible to implement using presently commercially-available components. Calculations show that approximately 200 million multiplications/second would be required, while presently commercially-available devices are believed only capable of about 20 million multiplications/second. Accordingly, it is believed that the structure shown in FIG. 12 cannot be used for high-quality audio signal conversion due to the state of present technology, although such systems have been used for voice-grade communications, where the bit rates are far lower. Accordingly, the two-stage digital filtering approach of FIG. 8 is preferred for overcoming this problem, as will be more evident hereinafter.

Referring again to FIG. 8, in order to reduce the number of multiplications/second required, the filter 106 is preferably a simple low-pass filter with relatively poor attenuation in the stop band region, e.g., above 20

KHz. The output of filter 106 is sampled by sampler 108 at an intermediate sample rate or frequency $f_2$ somewhere between the rate $f_1$ of the output of converter 104 and the final desired rate $f_3$. For example, where $f_1=6.144$ MHz and $f_3=48$ KHz, then a satisfactory value of $f_2$ is 96 KHz or twice $f_3$. The transmission characteristics of filter 106 should include a relatively flat response in the band of interest, e.g., 0-20 KHz, and provide sufficient attenuation of signal energy at frequencies between $f_1$ minus the bandwidth of interest and $f_2$ plus the bandwidth of the interest, e.g., 76 KHz-116 KHz, to avoid excess noise in the band of interest due to aliasing.

Once the word or sampling rate of the digital signal has been reduced to the word or sampling rate $f_2$, the signal can then be easily filtered by the second digital filter stage 110 and sampled by second sampler 112 for reducing the sampling rate to the desired rate $f_3$. Filter stage 110 functions to allow the resampling of the signal at the desired word rate $f_3$ by attenuating components above one-half the rate $f_3$, e.g., 24 KHz. Filter 110 also serves as an anti-aliasing filter to prevent analog input signals with components above $f_3/2$ from causing aliasing components to appear in the band of interest. Filter stage 110 preferably includes a finite impulse response (FIR) filter of the type having steep attenuation characteristics and a linear phase response. Since the analog filter 102 attenuates signals above 76 KHz (96 KHz-20 KHz) and preferably begins attenuating above the frequency band of interest, e.g., above 20 KHz, the second digital filter stage 110, although having a response that rises again at higher frequencies due to aliasing, will not alias due to the absence of this energy.

The converter shown and described with respect to FIG. 8 is described in greater detail with regard to FIGS. 13-22.

Figure 13:
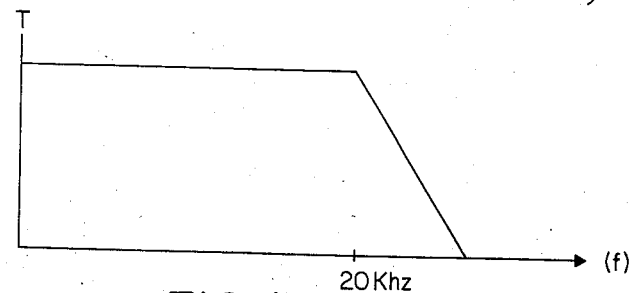
FIG. 13 is a simplified graphical representation of the transmission characteristics of the analog filter of the FIG. 8 embodiment.

The analog filter 102 may be any type of filter for sufficiently attenuating the signal energy above 76 KHz (96 KHz-20 KHz) as previously described. An example of the filter 102 is shown in FIG. 13, wherein the curve is flat up to 20 KHz and attenuates above 76 KHz. The cutoff frequency of the filter is preferably at 20 KHz and the filter preferably has at least 40 dB of attenuation above 76 KHz.

Figure 14:
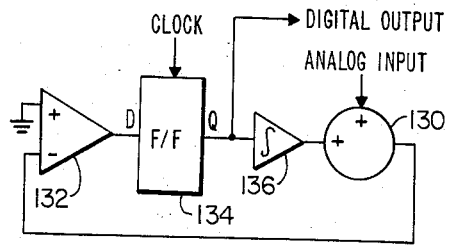
FIG. 14 is a block diagram of one embodiment of a topology useful for the high-speed converter of the FIG. 8 embodiment.
Figure 15:
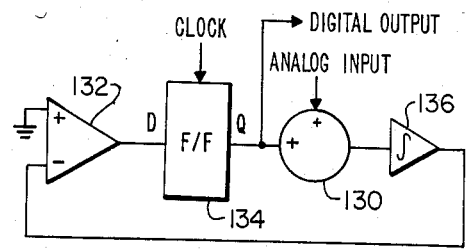
FIG. 15 is a block diagram of the preferred embodiment of a topology useful for the high-speed converter for the FIG. 8 embodiment.

The high-speed converter 104 preferably is an extension of a class of converters known as "sigma delta modulators". FIGS. 14 and 15 illustrate what are believed to be the two most common delta-modulator topologies. In FIG. 14, the analog input is applied to summer 130. The output of summer 130 is applied to the inverting input of a comparator 132 whose other input is referred to ground, and (i.e., signal inverter) 132, which in turn has its output applied to the D input of D flip flop 134. The latter is clocked with a clocking signal and provides at its Q output a high binary weighted signal (1) when the output of comparator 132 is positive at the time a clocking pulse is provided to the flip flop and low binary weighted signal (0) when the output of comparator 132 is negative and a clocking pulse is provided to the flip flop. The Q output of flip flop 134 forms the digital output at the clocking frequency and is also applied to a low-pass filter in the form of integrator 136 (having infinite DC gain), which in turn provides an output connected to the summer 130.

The analog input signal is thus summed with the output of integrator 136. A relative feedback path is formed via comparator 132, flip flop 134 and integrator 136. With no analog input signal, the system oscillates with a binary high to low signal ratio of approximately 1 to 1. If the integrator 136 is replaced by a properly designed low-pass filter, this oscillation will form a psuedo-random binary sequence and the spectrum of the oscillating signal at the input of comparator 132 will be white.

If a positive or negative analog input signal is next applied to the input of summer 130, the ratio of binary high to low signals will change in a direction to counteract the input signal. Thus, when the analog input signal is positive, this results in the digital output signal comprising a series of consecutive lows, decreasing the ratio of binary high to low signal until the output of integrator 136 is equal and opposite to the analog input signal. Conversely, when the analog input signal is negative, the digital output signal comprises a series of consecutive highs increasing the ratio of binary high to low signals until the output of integrator 136 is equal and opposite to the analog input signal. Since the integrator 136 has infinite DC gain, the ratio of binary high and low signals will return to 1 to 1 after the output of integrator 136 has reached a value sufficient to cancel the analog input signal at the summer 130.

The digital output of the converter of FIG. 14 is proportional to the slope of the analog input signal due to the presence of integrator 136 in the feedback loop, making it a slew-rate-limited system. The spectrum of the digital output is, therefore, a differential (6 dB/octave rising response) version of the input spectrum and can be decoded by simple integration. The spectrum of the noise at the decoded output is white, and the maximum signal level before overloading occurs is a linearly decreasing function of frequency.

While the topology shown in FIG. 14 can be utilized, the topology shown in FIG. 15 is preferred. The topology is similar to that shown in FIG. 14, except the summer 130 and integrator 136 are connected in reverse order so that the analog input signal is summed into the input of the integrator 136 rather than the output of the integrator. This results in the spectrum of the input signal appearing directly at the digital output of flip flop 134. The digital output signal can now be decoded by filtering out-of-band components above the frequency band of interest, e.g., 20 KHz. The maximum input level is now constant with frequency, but the spectrum of the noise floor has a 6 dB/octave rising characteristic. Both of the FIGS. 14 and 15 both provide the same signal-to-noise ratio at a particular frequency. The topology shown in FIG. 15 is not, however, slew limited but instead is amplitude limited. Therefore, the converter 106 preferably employs the topology of FIG. 15 in a "stacked" form. This is best illustrated in FIG. 16.

As shown, the A/D converter is of a parallel approximation type, wherein a plurality of resistors 138m, 138m-1 . . . 138A, 138B, 138C, 138D, . . . 138n-1, and 138n provide a resistor ladder with the middle of the ladder connected to system ground and the ends of the ladder connected respectively to equal, but opposite, positive and negative DC reference voltages. The junction of each pair of adjacent resistors are connected to the non-inverting input of a corresponding comparator 132. The value of end resistors 138m and 138n are identical to one another and dependent upon the amplitude of the DC reference voltages. The remaining resistors 138m-1 . . . 138n-1 are identical so that equal incremental voltages are applied and provide reference voltages to the non-inverting inputs of the comparators. Each digital output signal is applied to summer 130A, as well as to an input of a standard priority encoder 140. The output of summer 130A is applied to the low-pass filter which may be in the form of integrator 136A. The latter provides the other input signal to each of the inverting inputs of comparators 132. Each flip flop 134 will provide a high or low signal depending upon the value of the output of integrator 136A, as compared to the reference voltages provided by resistors 138, each time the flip flops 134 are clocked by the 6.144 MHz signal. It will be appreciated that by connecting the topology of FIG. 15 in parallel branches, as shown in FIG. 16, the dynamic range of the converter is increased with the addition of each branch. The converter of FIG. 15 can be, therefore, viewed as a 1-bit quantizer while the FIG. 16 arrangement is a "flash" converter arrangement. The number of comparators (i.e., the number of branches), therefore, can vary depending upon the dynamic range desired. In the preferred embodiment, the number of branches used is 15 so as to produce a 4-bit output of encoder 140. Specifically, if the number of branches used is represented by N so that N comparators 132 and N flip flops 134 are used, the loop "error" signal generated in each feedback path is quantized to N+1 values, and the dynamic range increases linearly with N.

The digital outputs of the flip flops 134, directly representative of the analog input signal, are preferably converted into a suitable binary format of 4 parallel binary signals by the priority encoder circuit 140 in a manner well-known in the art. Where 16 comparators are used to ultimately produce an 18 parallel bit output at 114 of FIG. 18, the dynamic range achieved is about 105 dB. The clock rate for flip flop 134 needed to achieve this dynamic range is 6.144 MHz.

Figure 16:
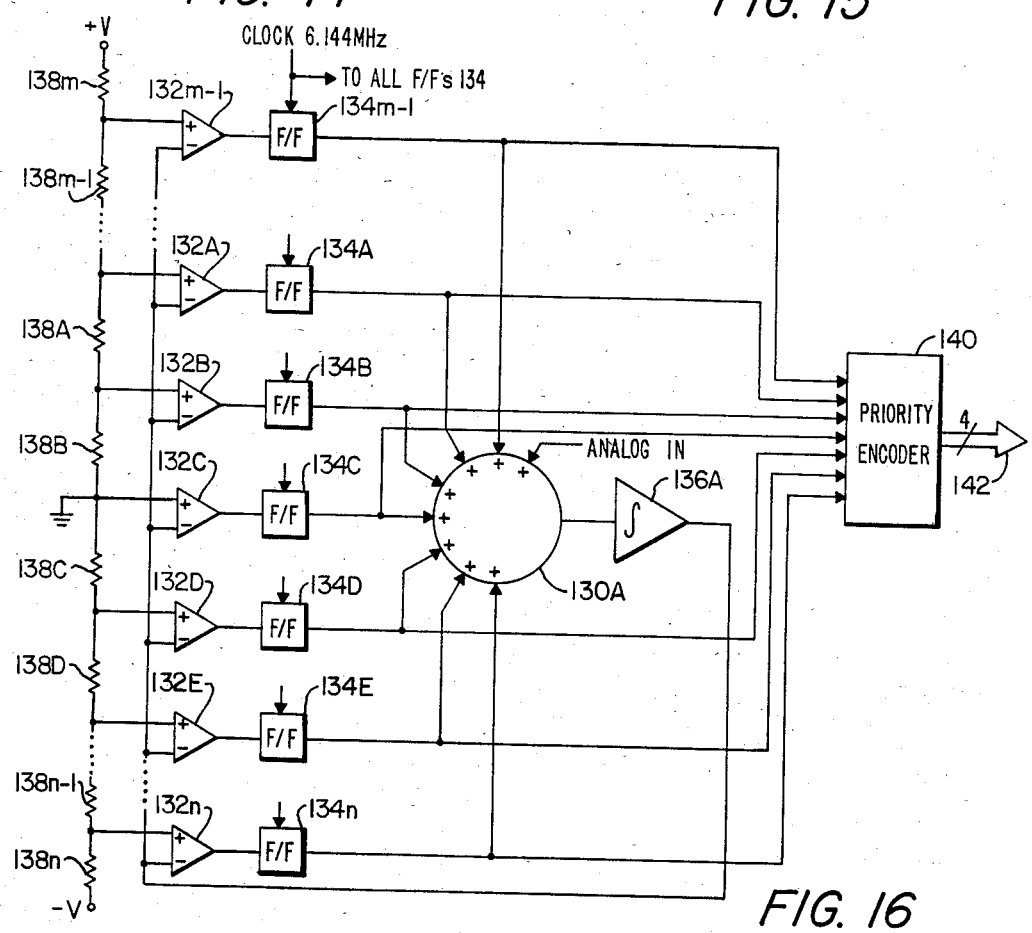
FIG. 16 is a block diagram of the preferred embodiment of the high-speed converter of the FIG. 8 embodiment.

The 4 parallel binary signals at 142 in FIG. 16 are applied to the two-stage digital filter, including the filter stages 106 and 110 and samplers 108 and 112. The first stage 106 and sampler 108 are used to resample the 4-bit binary output signal at a lower sampling rate of 96 KHz and is designed to keep out-of-band noise and signal energy from aliasing into the audio band so as to respectively prevent additional noise and spurious tones in the audio bands.

With output from the priority encoder 140 of FIG. 16 being at a relatively high rate, i.e., 6.144 MHz, a fairly simple digital filter is used. Generally, the preferred digital filter is of the type adapted to multiply, in each sampling interval, a sequence of past values of the digital signal by weighting coefficients, as is common. The weighting coefficients of the present invention are equal to integer powers of two, wherein the integer used is any integer including zero. Preferably, a series of "averaging" filter sections are used, wherein each output value is simply the sum of some finite number of past values of the input sequence so as to increase the resolution and attenuate of the high-frequency portions of the signal. The weighting coefficients in such a filter will be $2^0$ or 1. This relationship can best be described by the following equation (1) relating to the input sequence $X(N)$ to the output sequence $Y(N)$ for an averaging length of Q:

$$Y(N) = \sum_{P=N-Q+1}^{P=N} X(P) \quad (1)$$

Equation (1) implies that Q additions are required to compute every output sample. However, Equation (1) can be rewritten as follows so as to provide considerable savings in computation:

$$Y(N) = \left[ \sum_{P=N-Q}^{P=N-1} X(P) \right] + X(N) - X(N-Q) \quad (2)$$

$$Y(N) = Y(N-1) + X(N) - X(N-Q) \quad (3)$$

Equation (3) reveals that each new value of the output sequence $Y(N)$ can be computed by maintaining an average of the Q samples, and with each new input sample, adding each new input value to the average and subtracting the value of the input sampled Q sample intervals ago. Thus, it is not necessary to add all Q input samples with each new input value to compute each output value.

Figures 17, 18, 19:
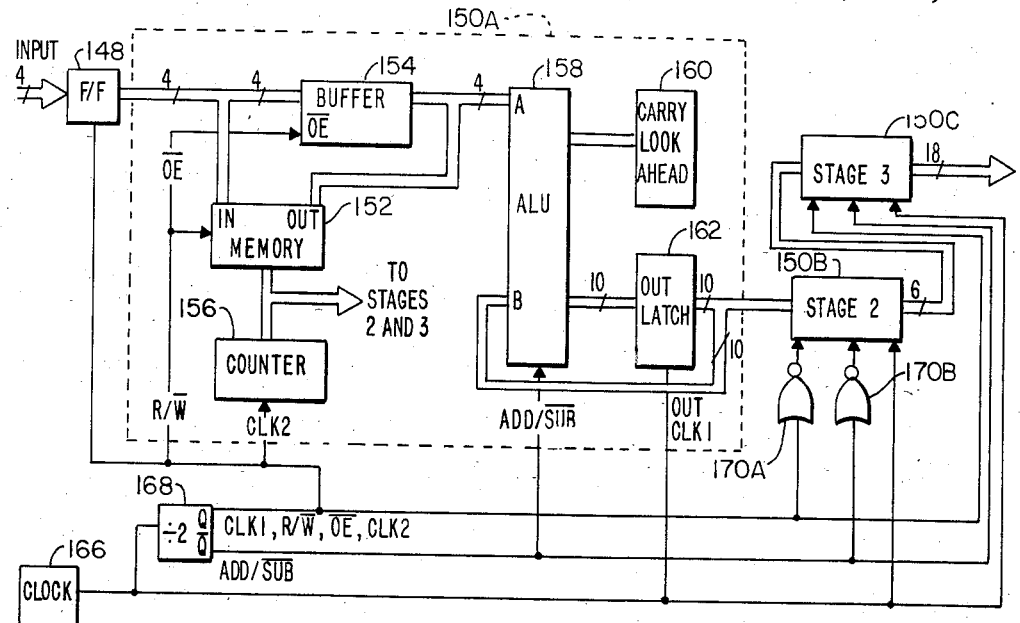
FIG. 17 is a block diagram of the preferred embodiment of the first section of the first digital filter stage of the FIG. 8 embodiment.
FIG. 18 is a graphical illustration of the frequency response of one filter section of the first digital filter stage.
FIG. 19 is a graphical illustration of the combined frequency response of three filter sections of the first digital filter stage.
Figure 20:
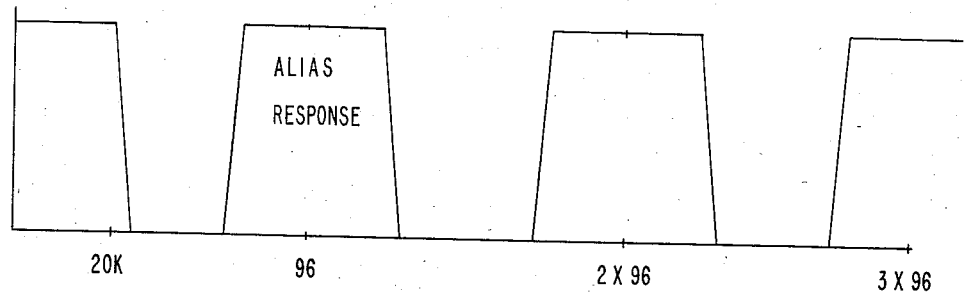
FIG. 20 is a graphical illustration of the frequency response resulting from sampling the signal at 96 KHz.
Figure 21:
FIG. 21 is a graphical illustration of the combined frequency response of the first and second digital filter stages.

The prefered embodiment of the first filter stage 106 of the FIG. 8 embodiment is shown in greater detail in FIG. 17. The 4-bit binary word output of the converter 104 is applied to the input of D flip flop 148, controlled by the clocking signal CLK1, preferably at the 6.144 MHz rate. The output of flip flop 148 is connected to the input of a first filter section 150. The input of filter section 150 is connected to the input of random access memory (RAM) 152 and the input of tri-state buffer 154. RAM 152 and buffer 154 are controlled by the same control signal (at the 6.144 MHz rate) designated R/$\overline{W}$ for RAM 152 and $\overline{OE}$ for buffer 154. When this control signal is low, the buffer 154 is in a low impedance state and, therefore, conductive, while RAM 152 is in a write state, and adapted to write data from the output of flip flop 148 into memory. When the control signal is high, the buffer 154 reverts to a high impedance state and is, therefore, nonconductive, while RAM 152 is in a read state and adapted to read (transmit) data from memory through its output.

RAM 152 stores each 4-bit word from flip flop 148 for Q sample intervals (chosen in the preferred embodiment as 64) before it reads the word out. This is controlled by the address counter 156, the latter preferably being a 6-bit (64) counter clocked by the CLK2 clocking signal at the 6.144 MHz rate.

The 4-bit word outputs of RAM 152 and buffer 154 are provided to the A input of an arithmetic logic unit (ALU) 158. The latter has A and B inputs and, as well-known in the art, will provide an output equal to the sum of the signals at its A and B inputs when a high ADD/$\overline{SUB}$ control signal is applied to its control input, and the difference between the signals at its A and B inputs (B-A) when a low ADD/$\overline{SUB}$ is applied to its control input. The A input of ALU 158 is connected to receive the output from RAM 152 when the latter is in its read state, and the output from buffer 154 when RAM 152 is in its write state. The carry look ahead unit 160 is used to carry out the addition and subtraction, as is well-known. The results of each addition and subtraction is step-accummulated in the output latch 162. The latch 162, therefore, contains the sum of the most recent 64 samples which is received from the output of the ALU. Such a sum will be represented by 10 bits [4 bits × 64(6 bits) = 10 bits]. The latch 162, when clocked by the OUTCLK1 signal during each sampling interval, provides the 10-bit binary output signal to the B input of the ALU 158 as the new 64 sample sum for the next sample interval. A 12.288 MHz clock 166 is used to generate the OUTCLK1 signal and an input to the divide by two 168. The latter provides the CLK1, R/$\overline{W}$, $\overline{\text{OE}}$ and CLK2 signals at one-half the 12.288 MHz frequency and the ADD/$\overline{\text{SUB}}$ at the 6.144 MHz, 180° out-of-phase from the CLK1, R/$\overline{\text{W}}$, $\overline{\text{OE}}$ and CLK2 signals.

The frequency response H(F) of this filter section 150A is well-known and is given by the following equation:

$$H(F) = \frac{\operatorname{Sin}(Q\pi F)}{\operatorname{Sin}(\pi F)} \qquad (4)$$

wherein

Q = the averaging length, (in the preferred embodiment = 64); and

F = input signal repetition rate or frequency.

The response, as shown in FIG. 18, is zero at regular intervals with the first zero occurring at (sampling rate/Q), e.g., 96 KHz, the second zero at twice the sampling rate/Q, e.g., 192 KHz, and zeros occurring at each multiple of the sampling rate/Q.

In FIG. 19, frequency regions centered about multiples of 96 KHz must be attenuated by the filter stage to prevent noise from aliasing into the audio band (below 20 KHz) if sampling is to occur at 96 KHz. It should be evident that the frequency regions which must be attenuated, are regions where the filter section has its greatest attenuation. However, the single filter section does not provide sufficient stopband attenuation to prevent excessive amounts of noise from aliasing into the audio band. This problem is overcome by using three filter sections 150 identical to filter section 150A, connected in series, as shown in FIG. 17, so that the frequency response H(F) becomes:

$$H(F) = \left[ \frac{\operatorname{Sin}(Q\pi F)}{\operatorname{Sin}(\pi F)} \right]^3 \qquad (5)$$

This response, shown in FIG. 19, will eliminate all of the alias response signals.

The three sections 150A, 150B and 150C, centered at each multiple of 96 KHz, are synchronized with the same control signals from clock 166 and divide by two 168, except that the CLK1, R/$\overline{\text{W}}$, $\overline{\text{OE}}$, CLK2 and ADD/$\overline{\text{SUB}}$ signals must be shifted by 180° with each subsequent filter section to properly time the availability of each new input signal to each filter section. Accordingly, inverters 170A and B are used to shift these control signals for the second filter section 150B. The third filter section does not require inverters, since a 360° phase shift from the original signals will be identical to the original signals.

Figure 23:
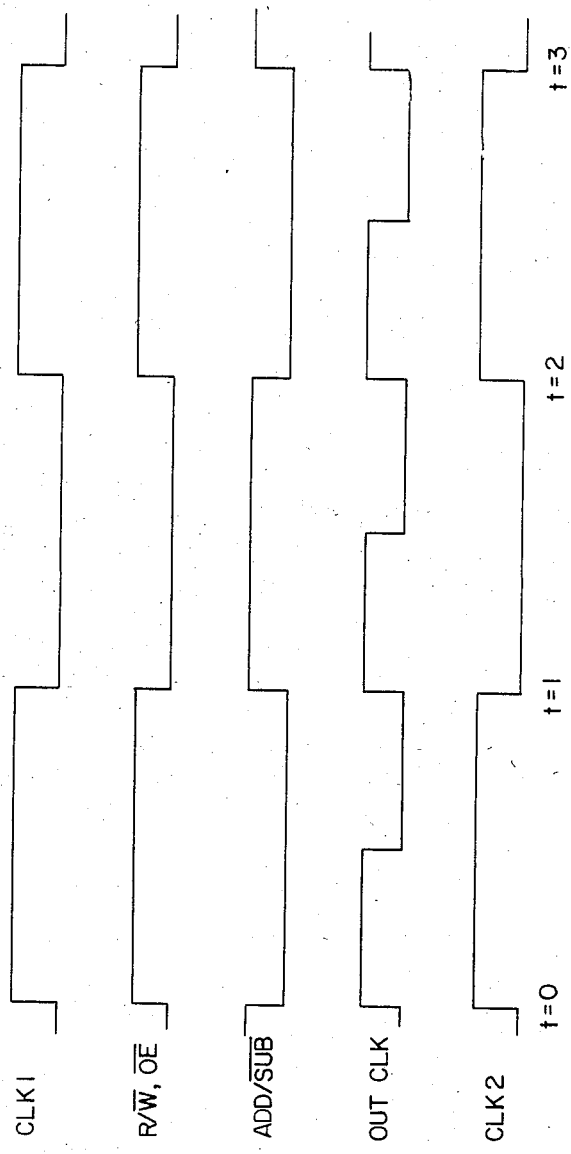

The operation of these three filter sections 150 will be better understood with reference to the timing diagram of FIG. 23. Specifically, the incoming 4-bit signal from the A/D converter is provided to flip flop 148. The latter is used to synchronize the incoming signal with the filter sections 150. At some preselected time t = 0, the CLK1, R/$\overline{\text{W}}$ and $\overline{\text{OE}}$ signals will go high, while the ADD/$\overline{\text{SUB}}$ signal goes low. The positive transition of CLK1 results in the 4-bit input to the flip flop 148 appearing at the latter's output. The CLK2 signal advances the counter 156 of each filter section 150 so as to address the locations in the RAM 152 sequentially through 64 locations. Counter 156 is clocked so that each incoming sample will be written into the particular location of RAM 152 at which a sample was last read out to ALU 158. The incoming sample will be stored for 64 sampling intervals, when the counter 156 completely recycles. During the read phase of RAM 152, when the R/$\overline{\text{W}}$ line is high, the delayed sample is provided at the output of RAM 152 and the buffer is non-conductive. The ADD/$\overline{\text{SUB}}$ signal is low so that the ALU 158 is in the subtract mode (will subtract the binary signal value at input A from the binary signal at input B). At this initial time t = 0, the OUTCLK1 signal will be high to output latch 162 so that the output of latch 162 (the 10-bit binary signal representative of the sum of the past 64 sample values), will appear at the B input of ALU 158, as well as to the input of the next filter section 150B. The value at the output latch 162 will now become the intermediate binary value resulting from this subtraction. At t = 1, the OUTCLK1 signal provides another positive transition, the R/$\overline{\text{W}}$ and $\overline{\text{OE}}$ signals will now go low and the ADD/$\overline{\text{SUB}}$ signal will go high. This results in the buffer 154 being set in a low impedance state, the RAM 152 set in a write mode and the ALU 158 set in the addition mode. The 4-bit word appearing at the output of flip flop 150 is thus written into RAM 152 at a location from which the last sample has been read out. This 4-bit output is also transmitted through buffer 154 to the A input of ALU 158. At the time t = 1, when the OUTCLK1 provides a positive transition, the intermediate value of the output of latch 162 is transmitted to the B input of ALU 158. The two signals are added together to provide a new value between t = 1 and t = 2 representative of the sum of the past 64 sample values provided to flip flop 148. Since the clocking signals R/$\overline{\text{W}}$, $\overline{\text{OE}}$, CLK2 and ADD/$\overline{\text{SUB}}$ of each successive section 150 are 180° delayed, the intermediate value output at t = 1 provided by the first filter section 150A will not be used by the next section 150B, since the RAM 152 of the second section 150B will be in a read mode and buffer 154 of the second filter section will be in a high impedance state by virtue of inverters 164A and 164B. It should be appreciated that when the converter initially starts, the RAM is cleared of all values and for the first 64 intervals during the subtract mode of ALU 158 the signal applied to input A will represent zero value so that the computations will not be affected.

The output of the first section 150A will thus still be at the 6.144 MHz rate, although each value of the output of the first section for each sampling interval will be representative of the average values of the previous 64 intervals. The output of the second filter section 150B for each sampling interval will be at the 6.144 MHz rate and will be representative of the average values of the output of the first filter section for the previous 64 intervals. Similarly, the output of the third section 150C for each sampling interval will be at the 6.144 MHz rate and will be representative of the output of the second section 150B for the previous 64 intervals. In this regard, the output of the second filter section 150B will be 16 bits, while the third filter section will have a resolution as high as 22 binary bits. Where fewer bits are required, e.g., 18 bits, some of the least significant bits of the output of filter section 150C can be ignored.

The output of filter section 150C is applied to the input of sampler 108, which in turn provides the input to filter stage 110. Sampler 108, filter stage 100 and sampler 112 of the preferred embodiment are shown in greater detail in FIG. 22. The filter is an FIR decimation filter adapted to read in every 64th sample (thereby reducing the sampling rate to 96 KHz) and to change the resulting sampling frequency from 96 KHz to the standard 48 KHz rate. The original sampling frequency of 96 KHz is thus reduced by a decimation factor of 2 although it will be obvious that any decimation factor can be provided.

Figure 22:
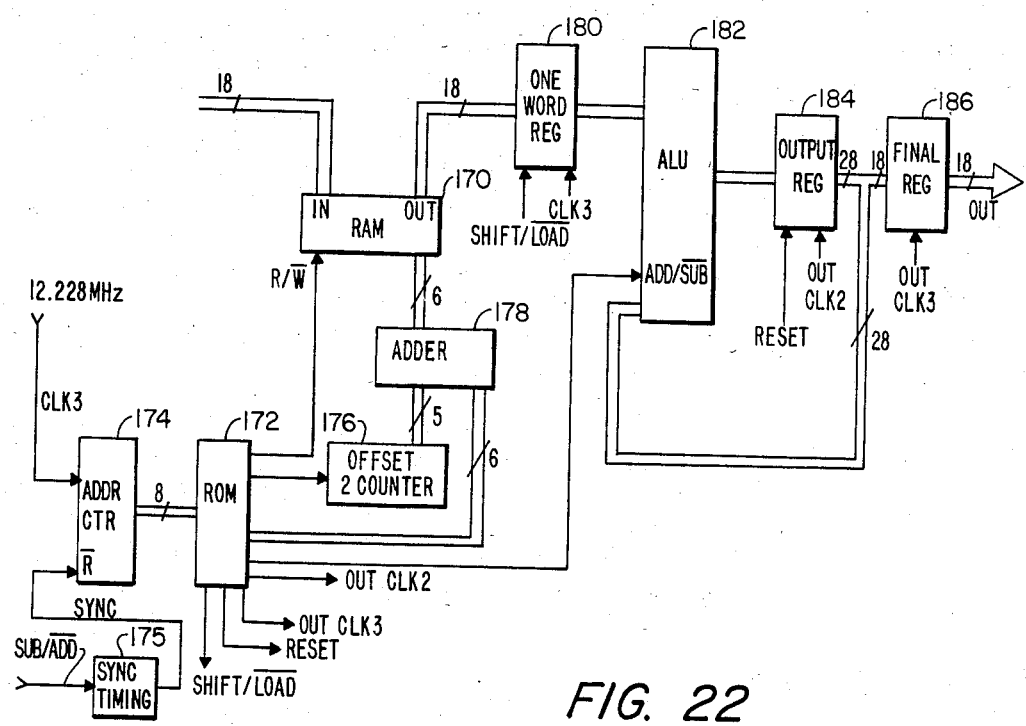
FIG. 22 is a block diagram of the preferred embodiment of first sampler, second digital filter stage and second sampler of the FIG. 8 embodiment.

The preferred filter 110 shown in FIG. 22 is a linear phase filter, designed to provide a data path wide enough to accommodate the data provided from filter section 150C, which in the embodiment described, is 18 bits. The filter functions as a tapped delay line and includes the RAM 170 having its input coupled to the output of the section 150C so that every 64th 18-bit word is parallel-loaded from the section 150C into the RAM 170. The RAM 170 is controlled by read only memory (ROM) 172, the latter providing the R/$\overline{W}$ control signal to the RAM. ROM 172 may be any commercially-available type of ROM, such as DM745287, manufactured by National Semiconductor, of Santa Clara, Calif., and programmed in a manner well-known in the art. ROM 172 also includes a coefficient look-up table, which is determined in a manner well-known in the art. The cutoff frequency of the filter is designed to be one-quarter the incoming sampling rate, i.e., one-quarter the 96 KHz rate or 24 KHz, so that about one-half of the coefficients become zero and the number of computations are reduced.

An address counter 174 provides an 8-bit address signal to the ROM 172 so that the program sequence of 256 steps can be sequentially carried out. The clocking signal, preferably a 12.288 MHz clocking signal, CLK3, and the counter reset signal, SYNC, are respectively provided by clock generator 166 and SYNC timing block 175 to the corresponding two inputs of the counter 174.

RAM 170 is addressed by ROM 172 through offset counter 176 and ADDER 178. Specifically, ROM 172 provides the 6-bit ROM address sequence directly to ADDER 178 for computing an output sample of the filter stage. The offset counter 176 receives a signal from ROM 172 for providing a 5-bit signal to ADDER 178 with each new address sequence for each new computation. The actual 6-bit signal sequence provided to RAM 170 (derived by adding each address of the sequence with the value provided by the offest counter 176) will be the same sequence when computing each output signal, except that the address sequence will be advanced by two with each new computation, all of which will be more evident hereinafter.

The word output of RAM 170 is coupled to the word register 180 adapted to store each 18-bit word output of RAM 170 when the SHIFT/$\overline{LOAD}$ signal received from ROM 172 goes low and the CLK3 signal from ROM 172 is provided. The output of register 180 is connected to the A input of ALU 182. The latter receives an ADD/$\overline{SUB}$ control signal from ROM 172. The output of ALU 182 is connected to the input of output register 184. The latter has its output connected to the B input of ALU 182 and to the input of final register 186. Output register 184 will provide an output signal when clocked by the ROM 172 with the OUTCLK2 and will be cleared when receiving the RESET signal from the ROM 172. The final register 186 provides an output signal when receiving the OUTCLK3 signal from ROM 172.

In operation, the incoming data word is received from filter section 150C and every 64th data word is parallel-loaded into specific address locations in RAM 170. The ROM 172, addressed by counter 174, provides the low R/$\overline{W}$ signal so that every 64th word is loaded into the RAM memory 170. The RAM 170 will next be addressed by adder 178 with the first address of an address sequence determined by ROM 172 and offset counter 176 and the word stored at that location will be entered into register 180. Next, the word in register 180 is multiplied by the first coefficient stored serially in the coefficient look-up table in ROM 172. A shift and add algorithm is used in ROM 172 to multiply the first coefficient by the data word in register 180. Such algorithms are well-known and thus the whole sequence will not be described. Generally, the shift and add algorithm will first determine whether each sequential bit of a coefficient forming the multiplier is a binary 1 or a binary zero. If the bit is 1, the contents of register 180 are added to the contents of register 184 by providing a high ADD/$\overline{SUB}$ signal to the ALU 182 when the CLK3 and OUTCLK2 signals are generated. A high SHIFT/$\overline{LOAD}$ signal is then provided to register 180 to shift the data word by 1-bit location. Should the coefficient bit be a zero, then the contents of register 180 will not be added to the contents of register 184. Each state of each bit of the coefficient is determined and the algorithm is carried out. The results of this first multiplication which is accumulated in output register 182. The next address of the sequence is provided by adder 178 to the RAM, and the stored data word is entered into register 180. The next coefficient is used in the look-up table as the multiplier and the word in register 180 as the multiplicand. The shift and add algorithm is used to accumulate the sum of the last product and the present product in register 184. When one-half of the address sequence is completed, the next sample from filter section 150C is ready to be entered into RAM 172. The same is written into a prescribed location in memory, and the address sequence continues until all of the computations are completed. The accumulated results in register 184 are now clocked into REG. 186 by the CLK3 signal. At this time, another sample is written from the filter section 150C into the RAM 170. In this manner, the output sampling rate is reduced to the desired 48 KHz rate. The ROM will then advance the offset counter input by two so that the sequence provided by ROM 172 will repeat itself, but the adder 178 will advance each address provided to RAM 170 by two. The foregoing will be better understood by the following example:

If the RAM includes 64 word storage locations, arbitrarily numbered 1-64, and 40 of the 64 data words stored in RAM are used for the computation of each output sample, the sequence may be as follows:

During the first interval at the 96 KHz rate a data word may be written into location 63. This operation is represented as W63. The word at the next location is read out, at location 1 (R1). This word is multiplied by coefficient 1 (R1C1). The sequence proceeds with R2, R2C2 and the sum R1C1+R2C2 is now accumulated in register 184. The sequences continues through R20 and R20C20, where R20C20 is added to the accumulated contents of register 184. W64 next occurs and the sequence continues with R21, R21C21, with R21C21 added to the contents of register 184. The sequence proceeds through R40, R40C40, with R40C40 added to the contents of register 184. These contents are then clocked out of register 184 into REG. 186 as an output sample. The address sequence is then advanced by clocking counter 176, and the next operation is a W1 followed by an R3, R3C3, etc. The final register 186 will provide the 48 KHz, 18-bit output signal.

Although not shown in FIGS. 8–23, the preferred system described also includes a power source for provided the necessary power for processing the analog input signal to produce the digital output signal and suitable means, such as a one-shot multivibrator, for generating a clear signal to all of the appropriate components of the system for clearing the components of all stored signals when the device is turned on by the power source.

The A/D converter thus described overcomes the problems of the prior art and thus provides improved resolution without the need for providing sophisticated anti-aliasing filters. The converter is capable of providing greater resolution than heretofore provided by 16-bit A/D converters. The converter provides fast and accurate conversion of analog signal to a digital signal without aliasing.

Since certain other changes may be made in the above apparatus without departing from the scope of the invention herein involved, it is intended that all matter contained in the above description or shown in the accompanying drawings shall be interpreted in an illustrative and not in a limiting sense.

I claim:

1. A device for converting an analog input signal to a relatively high resolution digital output signal representative of said analog input signal within a predetermined bandwidth, said device comprising:
    means for converting said analog input signal to a first relatively low resolution digital, signal at a first word repetition rate, said first digital signal being representative of said analog signal;
    signal generating means for generating said digital output signal at an output word repetition rate in response to and as a function of said first digital signal, said output word repetition rate being less than said first word repetition rate, said signal generating means comprising (1) means for generating an intermediate digital signal at an intermediate word repetition rate in response to and as a function of said first digital signal, said intermediate word repetion rate being less than said first word repetion rate and greater than said output word repetition rate, (2) means for minimizing aliasing resulting from the differences in said word repetition rates and (3) means for attenuating those portions of said intermediate digital signal representative of out-of-band signals and noise of said analog input signal outside said bandwidth.

2. A device according to claim 1, wherein said said means for converting said analog input signal to said first digital signal includes a delta modulator.

3. A device according to claim 2, wherein said delta modulator is amplitude limited.

4. A device according to claim 2, wherein said means for converting said analog input signal to said first digital signal includes a plurality of said delta modulators connected in a parallel stack arrangement so that the number of said modulators providing a digital signal is a function of said analog input signal.

5. A device according to claim 2, wherein said delta modulator is slew rate limited.

6. A device according to claim 1, wherein said means for generating said intermediate digital signal includes a digital filter stage, said digital filter stage being adapted to multiply said first digital signal by coefficients equal to $2^n$, where n=any integer including zero.

7. A device according to claim 6, wherein said each of said coefficients equals 1.

8. A device according to claim 1, wherein said means for generating said intermediate digital signal includes a digital filter stage for generating said digital signal such that the value of said intermediate digital signal for each sampling interval of said first word repetition rate is a function of the average values of said first digital signal for the just preceding sample intervals of said first word repetition rate substantially occurring over the time of a sampling interval of said intermediate word repetition rate.

9. A device according to claim 8, wherein said digital filter stage includes a recursive filter.

10. A device according to claim 9, wherein said signal generating means includes a second digital filter stage responsive to said intermediate signal, said digital filter stage including means for sampling said intermediate signal at said output word repetition rate.

11. A device according to claim 10, wherein said second digital filter stage includes a finite impulse response filter.

12. A device according to claim 11, wherein said finite impulse response filter is a linear phase filter.

13. A device according to claim 1, wherein said means for generating said intermediate digital signal includes a digital filter stage, said digital filter stage includes a filter section having a frequency response H(F) approximated as follows:

$$H(F) = \frac{\text{Sin}(Q\pi F)}{\text{Sin}(\pi F)}$$

wherein
    Q=the number of sampling intervals of said first word repetition rate substantially occurring within a sampling interval of said intermediate word repetition rate; and
    F=the word repetition rate of the input signal to said filter section.

14. A device according to claim 13, wherein said digital filter stage includes a plurality of said filter sections having substantially identical frequency responses H(F).

15. A device according to claim 14, wherein said digital filter stage includes at least three of said sections connected to one another in series.

16. A device according to claim 1, wherein the number of the sampling intervals of said first word repetition rate substantially occurring over the time of a sampling interval of said intermediate word repetition rate is represented by Q and said means for generating said intermediate digital signal includes a digital filter stage, said digital filter stage comprising a filter section, said filter section including second means for generating a digital output signal Y(N) of said filter section at the interval N at the first word repetition rate representative of the sum of the digital input signal X(P) to said filter section occurring between intervals P=N−Q+1 through P=N, said second means including means for storing an accumulated digital signal representative of the just preceding digital output signal Y(N−1) of said filter section, means for adding the digital input signal X(N) of said filter section and subtracting the value of said digital input signal X(N−Q) of said filter section from said accumulated digital output signal Y(N−1) of said filter section so as to produce said digital output signal Y(N), said intermediate digital signal being a function of and responsive to said digital output signal Y(N).

17. A device according to claim 16, wherein said digital filter stage includes a plurality of said filter sections connected in series.

18. A device according to claim 17, wherein said digital filter stage includes three of said sections.

19. A device according to claim 1, wherein said signal generating means includes a digital filter stage responsive to said intermediate signal, said digital filter stage including means for sampling said intermediate signal at said output word repetition rate.

20. A device according to claim 19, wherein said digital filter stage includes a finite impulse response filter.

21. A device according to claim 20, wherein said finite impulse response filter is a linear phase filter.

* * * * *

UNITED STATES PATENT AND TRADEMARK OFFICE
CERTIFICATE OF CORRECTION

PATENT NO. : 4,588,979
DATED : May 13, 1986
INVENTOR(S) : Robert W. Adams

It is certified that error appears in the above-identified patent and that said Letters Patent is hereby corrected as shown below:

Page 1, the designated assignee "DBX, Inc. of Newton, Mass." should be -- BSR North America Ltd.   New York, New York, Claim 1, column 15, line 32, delete "," after "digital";

Claim 1, column 15, line 44, delete "repetion" and substitute therefor -- repetition --;

Claim 1, column 15, line 45, delete "repetion" and substitute therefor -- repetition --; and Claim 2, column 15, line 53, delete "said".

Signed and Sealed this

Twenty-sixth Day of August 1986

[SEAL]

Attest:

DONALD J. QUIGG

Attesting Officer

Commissioner of Patents and Trademarks